United States Patent
Staloff (10) Patent No.: US 9,605,942 B2
(45) Date of Patent: Mar. 28, 2017

(54) OCT PROBES AND OCT OPTICAL PROBE COMPONENT FOR USE THEREIN

(71) Applicant: Corning Incorporated, Corning, NY (US)

(72) Inventor: Daniel Max Staloff, Rochester, NY (US)

(73) Assignee: Corning Incorporated, Corning, NY (US)

( * ) Notice: Subject to any disclaimer, the term of this patent is extended or adjusted under 35 U.S.C. 154(b) by 297 days.

(21) Appl. No.: 14/297,798

(22) Filed: Jun. 6, 2014

(65) Prior Publication Data

US 2015/0036146 A1     Feb. 5, 2015

Related U.S. Application Data

(60) Provisional application No. 61/860,562, filed on Jul. 31, 2013.

(51) Int. Cl.
    *G01B 9/02*     (2006.01)
    *A61B 1/00*     (2006.01)
    *A61B 5/00*     (2006.01)

(52) U.S. Cl.
    CPC ........ *G01B 9/02091* (2013.01); *A61B 1/0008* (2013.01); *A61B 1/00096* (2013.01); *A61B 5/0066* (2013.01); *A61B 5/0084* (2013.01); *A61B 1/00172* (2013.01); *A61B 1/00183* (2013.01)

(58) Field of Classification Search
CPC G02B 21/0028; G02B 6/0238; G02B 6/3841; G02B 13/0095; G02B 23/2446; G02B 23/26; G01B 9/02091; A61B 1/0008; A61B 1/00096; A61B 1/00183; A61B 1/00172; A61B 5/0066; A61B 5/0084
See application file for complete search history.

(56) References Cited

U.S. PATENT DOCUMENTS

| | | | |
|---|---|---|---|
| 5,770,847 A | 6/1998 | Olmstead | |
| 6,330,118 B1 | 12/2001 | Daschner et al. | |
| 6,445,939 B1 | 9/2002 | Swanson et al. | |
| 1,431,000 A1 | 6/2012 | Jeong et al. | |
| 2011/0218403 A1* | 9/2011 | Tearney | A61B 5/0066 600/165 |
| 2012/0143100 A1 | 6/2012 | Jeong et al. | |

OTHER PUBLICATIONS

International Search Report and Written Opinion of the International Searching Authority; PCT/US2014/048350; Mailed Oct. 7, 2014, 10 Pages; European Patent Office.

* cited by examiner

*Primary Examiner* — Joseph P Martinez
(74) *Attorney, Agent, or Firm* — Svetlana Z. Short

(57) ABSTRACT

An OCT optical probe component comprising: A rod having a first end and a second end, a lens situated proximate to the second end of the rod, the lens having a surface with an inner zone a, and an outer zone b, wherein the inner zone a is associated with the focal length fla, and said outer zone b is associated with the focal length flb, such that optical probe component is multi-focal, the optical probe capable of imaging at multiple image planes, via the lens of an object adjacent to the first end of the rod, wherein the at least two images are separated by a distance d, wherein d>1 mm.

20 Claims, 6 Drawing Sheets

OCT PROBES AND OCT OPTICAL PROBE COMPONENT FOR USE THEREIN

CROSS-REFERENCE TO RELATED APPLICATIONS

This application claims the benefit of priority under 35 U.S.C. §120 of U.S. Application Ser. No 61/860,562 filed on Jul. 31, 2013 the content of which is relied upon and incorporated herein by reference in its entirety.

BACKGROUND

The disclosure relates generally to probes for Optical Coherence Tomography (OCT), and more particularly to OCT probes which may be used in medical applications.

No admission is made that any reference cited herein constitutes prior art. Applicant expressly reserves the right to challenge the accuracy and pertinency of any cited documents.

SUMMARY

One embodiment of the disclosure relates to an OCT optical probe component comprises:
(a) an optically transparent rod having a first end, and
(b) a lens optically coupled to the rod, the lens having a surface with an inner zone a, and an outer zone b, wherein the inner zone corresponds to a focal length fla, and the outer zone corresponds to the focal length flb, such that the optical probe component is multi-focal, said optical probe capable of imaging via the lens an object (fiber core) adjacent to the first end of the rod at multiple image planes, wherein at least two images are separated by a distance d, wherein d>1 mm.

One embodiment of the disclosure relates to an OCT optical probe component comprises: a rod and a curved refractive surface, the refractive surface having an inner zone a defined by the radius of curvature r1a and an outer zone b defined by a radius of curvature r1b, wherein r1a is not equal to r1b, and the optical probe component is multi-focal. In some embodiments 100 µm≤r1a≤5000 µm; 100 µm≤r1b≤5000 µm; and |r1a−r1b|>2 µm.

According to some embodiments the optical probe component has a first end, a second end, and further comprises: (a) a light transmissive rod having a central axis; (b) a surface situated on the second end and slanted with respect to the central axis (preferably a total internal reflectance surface); (c) a lens element 25C situated on the rod 25A and being integral there to, and adjacent to the second end, the lens element having a curved refractive surface having an inner zone a defined by the radius of curvature r1a and an outer zone b defined by a radius of curvature r1b, wherein r1a is not equal to r1b such that the optical probe component is multi-focal. In some embodiments 100 µm≤r1a≤5000 µm; 100 µm≤r1b≤5000 µm; and |r1a−r1b|>2 µm.

In at least some embodiments an object (e.g., fiber core) that is located proximate to the first end of the rod is imaged via the lens on at least two locations separated by a distance d, such the distance d>2 mm, preferably greater than 3 mm, more preferably by at least 4 mm.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION

In optical coherence tomography (OCT) imaging information about biological tissues can obtained by medical scanning done inside a living body, by utilizing an OCT probe 5 that contains a small optical probe component 20 (also referred to herein as miniature optic sensor, or a micro optic component 20). The small optical probe component 20 images light provided by an optical fiber 21 onto the tissues, and collects the light scattered back by the tissues. For example the OCT probe 5 including an OCT probe assembly 10 containing the small optical probe component 20 coupled to the optical fiber 21 is inserted inside the body, for example through the blood vessels or gastro intestinal tract, to obtain an image of the inside surfaces of the tissues such as blood vessels, or tissues of the intestinal tract.

More specifically the OCT probe assembly 10 moves inside a body to obtain sub-surface 3D information of tissues. Light scattered back from the tissues (at different depths) is monitored using interferometric techniques, resulting in 3D scan of the tissues. The 3D scan is achieved by rotating and translating the optical probe component 20 and its housing 45 at high speeds (for example greater than 1000 rpm) in a controlled fashion. This rotation is achieved, for example, by using rotation/translation device 30, for example, a stainless steel coiled wire torque tube 30 (attached to the optical probe component 20, and/or optical fiber 21, or to the housing 45). The rotation/translation device 30 and the OCT probe assembly 10 that includes the optical probe component 20 and its housing 45 are then threaded through a close fitting transparent tube (e.g., made of polymer) referred to as an inner lumen 48. During OCT device operation, the OCT probe assembly 10 and the stainless steel coiled wire torque tube 30 rotate inside the transparent tube (cylinder) called the inner lumen 48, and the inner lumen 48 protects the tissues from contact with the rotating OCT probe assembly 10. The inner lumen 48, because of its cylindrical shape, produces optical aberration(s) that are corrected for with the optical probe component 20. Without correction for the aberrations introduced by the cylindrical shape of the inner lumen 48, the image quality is poor. A schematic of the OCT probe 5 including a portion of the torque tube, and the OCT probe assembly 10 situated in an inflatable balloon 8 is illustrated, for example, in FIG. 1.

Sometimes, various OCT applications require different working distances, to cover the possible range of esophageal diameters, organs with large surface or shape irregularity (for example, organs may have surfaces that may be located at different distances from the optical probe component). To image such surfaces one will need OCT probes that provide different working distances. The number of required probes could be reduced if the probe had a longer depth of focus.

OCT probe assemblies may be utilized in different environments, and in different environments the distances from the micro optic component 20 to the tissues that are being scanned are different. It is inconvenient and expensive to replace the OCT probe in order to provide a probe assembly that has optical probe component with a different working distance or different focal length. Different people, even for the same type of application, may require micro optic components with different working distances and/or focal length. For example, esophageal diameters may vary from person to person. Rather than requiring that the end user utilize different probes—each designed for a narrow range of working distances, and select the proper probe for each use, the embodiments of micro optic components 20 disclosed herein are a multi-focal and, therefore can be advantageously utilized to provide images situated at different distances from the optic components 20. That is, advantageously, optic components 20 can be utilized with a wider range of applications requiring different working distances because they have larger depth of focus. Additionally, producing an OCT scan of the tissues of an object of irregular shape, such as a bladder, would also be possible with multi-focal optic components 20 that have large depth of focus. Thus, the embodiments of multi focal optic components 20 provide one or more of the following advantages:

1) The multi-focal micro optic components 20 has an extended depth of focus, useful for providing light to objects with large surface irregularity;
2) When collecting returned scattered light, the multi-focal micro optic components 20 in conjunction with the optical fiber 21 (if the fiber is a single mode fiber) can filter out the out of focus light because it is utilised with the fiber that has small fiber core aperture;
3) The focal micro optic components 20 has large depth of focus which reduces the number of different probes needed by the end user.

Therefore, according to some embodiments, the OCT optical probe component 20 comprises: a rod 25A and a curved refractive surface 25B or 25C. In one cross-sectional view the refractive surface has the radius of curvature that changes from value r1a to value r1b. That is, refractive surface has an inner zone (also referred to as an inner region herein) a defined by the radius of curvature r1a and an outer zone b (also referred to as an outer region herein) defined by a radius of curvature r1b, wherein r1a is not equal to r1b and the optical probe component 20 is multi-focal. According to some embodiments $100 \ \mu m \leq r1a \leq 5000 \ \mu m$; $100 \ \mu m \leq r1b \leq 5000 \ \mu m$; and $|r1a-r1b| > 2 \ \mu m$. For example, $100 \ \mu m \leq r1a \leq 2500 \ \mu m$; $100 \ \mu m \leq r1b \leq 2500 \ \mu m$; and $|r1a-r1b| > 10 \ \mu m$. In some embodiments the OCT optical probe component 20 has the length L wherein $2 \ cm > L > 0.3 \ cm$ (where L is measured from a surface nearest the fiber end to the end of the probe nearest the lens or the reflective surface), and the rod 25A has a maximum diameter $D < 2$ mm. The maximum preferred overall length L' of the optical component 20 (including fiber mount 27 if it is integral thereto) is $3 \ cm > L' > 0.5 \ cm$, and preferably $2 \ cm > L' > 0.5 \ cm$, for example $1 \ cm > L' > 0.5 \ cm$. In some embodiment an object (fiber core 21A of the optical fiber 21) located proximate to the first end of the rod 25A is imaged via the curved refractive surface of the optical probe component 20 on at least two locations separated by a distance d, such the distance $d > 1$ mm, for example $> 1.5$ mm, preferably greater than 2 mm, more preferably greater than 3 mm, and even more preferably by at least 4 mm (e.g., 5 to 15 mm, or 6 mm to 10 mm). The OCT optical probe component preferably has the length L wherein $2 \ cm > L > 0.5 \ cm$ and the rod 25A has a maximum diameter $< 2$ mm. For example OCT optical probe component 20 may include a refractive surface that in one cross-section has at least two zones defined by the radii r1a and r1b wherein $100 \ \mu m \leq r1a \leq 5000 \ \mu m$; $100 \ \mu m \leq r1b \leq 5000 \ \mu m$; and $|r1a-r1b| > 2 \ \mu m$. That is, the refractive surface is defined by at least one cross-section a radius r1, such that r1 changes its values from the r1a (inner zone) to r1b (outer zone). If the optical probe component 20 is not designed to be utilized with the inner lumen, the curved refractive surface is preferably rotationally symmetrical—i.e., the radii of curvature is the same in two orthogonal directions. If the optical probe component 20 is designed to be utilized with the cylindrically shaped inner lumen 48, it is defined in another cross-section by at least another radius r2, such that r2 changes its values from the r2a (inner zone) to r2b (outer zone), and r2a<r1a and r2b<r1b. (I.e., if the inner lumen 48 is utilized with the optical probe component 20, the radii r2a, r2b, and r1a, and r1b are the radii of the curved surface that are measured in orthogonal directions, and the curved surface can be described as a part of a toroid because the radii in two orthogonal directions (even when measured at the same distance from the same vertex, are not equal to one another—i.e., r1a does not equal to r2a, and r1b does not equal to r2b). In some embodiments the outer radius Ra of zone a corresponds to the inner 0.2 to 0.5 of the clear aperture CA of the lens surface, and inner radius Rb of zone b may be situated in location between 0.3 the clear aperture of the lens surface (e.g., zone b may be situated in the location corresponding to 0.3 CA to 1 CA).

Figure 2:
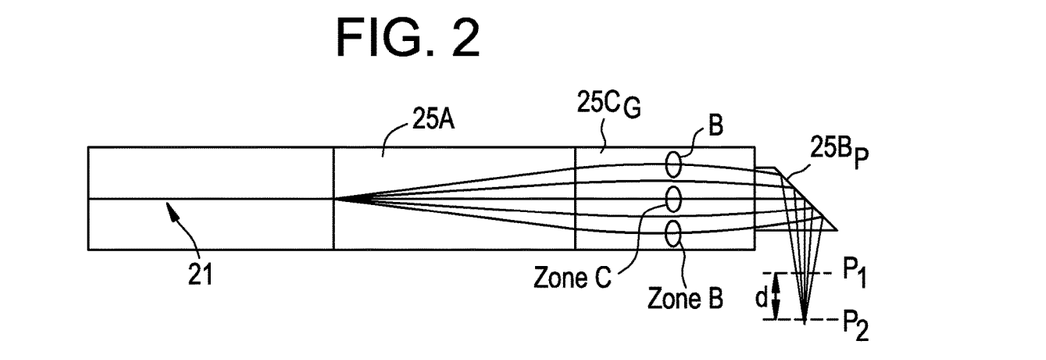
FIG. 2 is a schematic cross-sectional view of one embodiment of the optical probe component that utilizes a GRIN lens element.

Although according to some embodiments, the multi-focal OCT probe component may be made from a silica (optically transparent) spacer rod 25A, GRIN lens element 25C$_G$ (i.e., a lens element with a refractive index profile corresponding to multiple foci), and reflecting microprism 25Bp with the reflective surface 25B, as shown in FIG. 2. The different components of such micro optic component 20 including the GRIN lens element, the spacer rod, and the prism can be made of different materials. The GRIN lens includes a refractive surface with at least two zones, a and b, each associated with a different focal length f1a and f1b, therefore the image of the fiber's core will be formed on multiple image planes (corresponding to different working distances) that are spaced apart by a distance d, and the image planes associated with zones a and b will be separated by a distance d>1 mm. For example, image planes P1, P2 may be separated (or spaced apart) by a distance d where d>2 mm, for example d>3 mm, or d>4 mm, or d>5 mm. Also for example, if the GRIN lens $25C_G$ is made of a stepped index material, the lens's gradient index profile could have slightly different inner and outer zone index gradients (or different refractive indices) to achieve different focal lengths f1a and f1b corresponding to the inner and outer zones, and thus to different working distances. However, this architecture (i.e., making the multi-focal OCT probe component from several components that are either spaced apart or cemented together) can be difficult to manufacture because it has tight tolerances, especially for component thicknesses. Thus, preferably, preferably, according to some embodiments, the micro optic component 20 is a monolithic component with a refracting surface for providing optical power.

Figure 3:
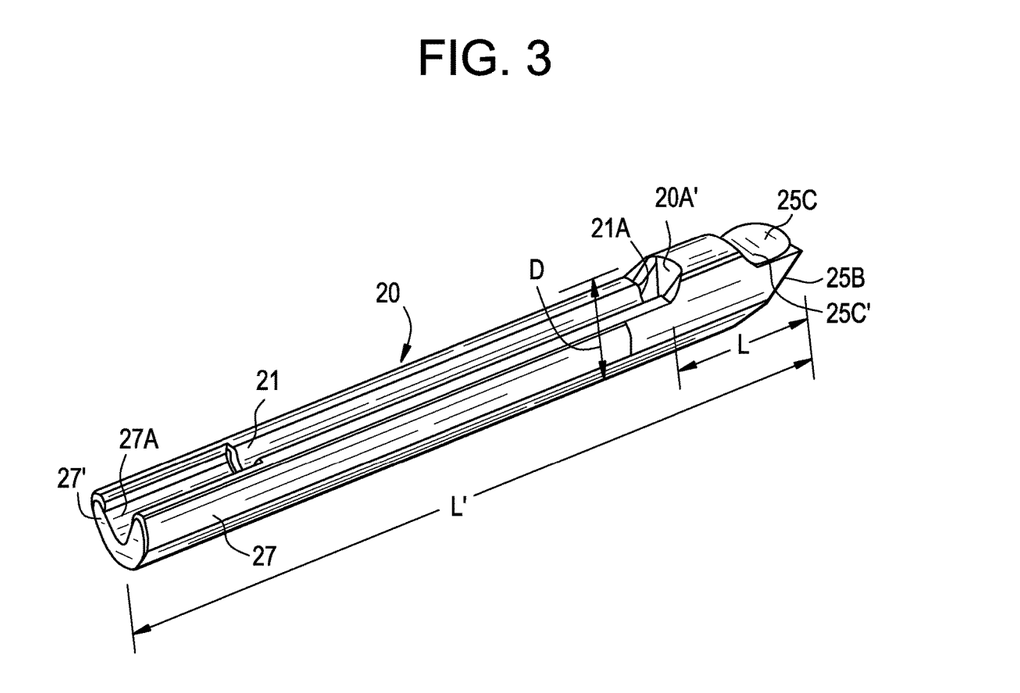
FIG. 3 illustrates another of one embodiment of the optical probe component.

With reference to FIG. 3, according to some embodiments the optical probe component 20 has a first end 20A' (situated next to the fiber 21), a second end 20A" and further comprises: (a) a light transmissive rod 25A having a central axis $25_{CA}$; (b) a surface 25B situated on the second end and slanted with respect to the central axis $25_{CA}$, wherein surface 25B is preferably a TIR (total internal reflectance) surface; (c) a lens element 25C situated on the rod 25A and being integral there to, and adjacent to the second end and to the 25B, the lens element 25C having a curved refractive surface 25C'. If the optical probe component will be situated within the inner lumen 48 (or is covered by a cylindrical window), than in order to correct for the aberrations introduced by the cylindrical shape of the inner lumen 48 (or the cylindrical window) the refractive surface 25C' has at least two changing radii of curvature r1, and r2 respectively in two orthogonal cross-sections, where r1 does not equal r2. That is, in one cross-section the radius of curvature is r1, and in the other cross-section r2. Preferably 100 µm≤r1≤5000 µm and 100 µm≤r2≤5000 µm (and in some embodiments. 300 µm≥r1≥1000 µm). Preferably the a lens element 25C has a thickness t, where 100 µm≥t≥3000 µm (for example, t may be 100 µm, 200 µmm, 300 µm, 500 µm, 750 µm, 1000 µm, 2000 µm, 2500 µm or therebetween). Lens element 25C of this embodiment is a split aperture (non-diffractive) lens.

Preferably, as described below, the radius r1 of the curved refractive surface 25C' changes its value from r1a to r1b to provide the required depth of focus, and preferably 500 µm>|r1a−r1b|>2 µm. More preferably 100 µm>|r1a−r1b|>10 µm. (Please note that r1a and r1b are measured in the same cross-section).

In the embodiments that do not utilize the inner lumen 48, the lens surface is rotationally symmetrical, i.e., r1=r2 and thus r1a=r2a, and r1b=r2b. In the embodiments that utilize the inner lumen 48, in order to compensate for the astigmatism introduced by the cylindrically shaped surfaces of the inner lumen 48, r2 is not equal to r1, thus r2a is not equal to r1a and r2b is not equal to r1b, for example, r2a<r1a and r2b<r1b. Thus, in some embodiments, the radius r2 of the curved refractive surface 25C' changes its value from r2a to r2b to provide the required depth of focus, and preferably 500 µm>|r2a−r2b|>2 µm, for example 100 µm>|r2a−r2b|>10 µm.

In this embodiment the optical probe component 20 is monolithic. The monolithic optical probe component 20 can, for example, be molded as one unitary (single) component of glass or plastic. Alternatively it can be manufactured, from the same optically transparent material (example, diamond turned glass or plastic). According to some embodiments, the OCT probe assembly 10 includes further includes a fiber mount 27 and an optical fiber 21 supported by the fiber mount 27.

However, if the optical probe component 20 is not used with the transparent cylinder—i.e., if it is not situated within the inner lumen or is not covered by a cylindrical window, the refractive surface 25C' can be rotationally symmetrical with respect to its radii of curvature. i.e., r1=r2, but the value r1 changes from r1a to r1b, as one moves from vertex to the edge of the lens surface).

The fiber 21 can be a single mode fiber, with a core diameter of preferably <8.5 µm, for example SMF-28E®, available from Corning Incorporated, of Corning, N.Y. The mount 27 is located adjacent to the rod 25A, the optical fiber 21 is optically coupled to the rod 25A and the housing 45, for example, surrounds the fiber mount 27 and at least a portion of the optical fiber 21 is supported therein. The fiber 21 may be in physical contact with the rod 25A or may be separated from it by a small air gap. According to some embodiments an index matching material or glue may be present in the space between the fiber 21 and the rod 25A. In some embodiments the mount 27 forms an integral part of the optical probe component 20 (see FIG. 3, for example).

As stated above, and shown in FIG. 3 in some embodiments the lens element 25C is integral to the optical probe component 20—that is, in these embodiments the lens element 25C is made from the same material as the rest of the optical probe component 20, i.e.,—the optical probe component 20 as two or more different components that were cemented to one another. As stated above, the fiber mount 27 preferably is also made integrally with the other elements of the micro optic component 20. The fiber mount 27 may include a v-grove 27A or a bore (not shown) to support the fiber 21 and an end 27' that is not proximate to the end 20' associated with the rod 25A. Thus, in the embodiment shown in FIG. 3, the micro optic component 20 (including the lens element 25B, the rod 25A, the slanted surface 25C) and the fiber mount 27 are made from the same material. That is, the micro optic component 20 is made as one unitary single component of glass or plastic, from the same optically transparent material (e.g., of diamond turned glass or plastic, or molded as one piece of glass or plastic).

According to some embodiments the optical probe component 20 has a first end 20A'(situated next to the fiber 21), a second end 20A" and further comprises: (a) a light transmissive rod 25A having a central axis $25_{CA}$ (the end 20A' corresponds to the end of the rod that faces the fiber); (b) a surface 25B situated on the second end and slanted with respect to the central axis $25_{CA}$, wherein surface 25B is curved and is coated with a reflective coating 25W, If the optical probe component 20 with the transparent cylinder, i.e., if it is situated within the inner lumen 48 (or is covered by a cylindrical window), than the surface 25B has two radii of curvature r1, and r2 in two cross-sections, where r1 does not equal r2, to correct for the aberrations introduced by the cylindrical shape of the inner lumen 48. That is, in one cross-section the radius of curvature is r1, where r1 does not have a constant value (e.g., r1 is r1a, or r1b, etc., depending on the lens aperture zone), and in the other orthogonal cross-section the radius of curvature is r2 (where r2 does not have a constant value (e.g., r2 is r2a, or r2b, etc., depending on the lens aperture zone). Preferably 100 µm≤r1≤5000 µm and 100 µm≤r2≤5000 µm (and in some embodiments, 300 µm≤r1≤2000 µm, or 300 µm≤r1≤1000 µm). That is 100 µm≤r1a≤5000 µm and 100 µm≤r1b≤5000 µm, where r1a corresponds to the inner zone a, and does not equal r1b which corresponds to the outer zone b. In this embodiment the optical probe component 20 is monolithic. The monolithic optical probe component 20 can, for example, be molded as one unitary (single) component of glass or plastic. Alternatively it can be manufactured, from the same optically transparent material (example, diamond turned glass or plastic. According to some embodiments, the optical probe component 20 includes further includes a fiber mount 27 for the optical fiber. Preferably, the curved surface 25B forms a split aperture lens (i.e., a lens with the inner zone a, and an outer zone b), and as described below, the radius r1 changes its value from r1a to r1b to provide the required depth of focus. Thus the optical probe component 20 is a multi focal component. For example 500 µm>|r1a−r1b|>2 µm, and the corresponding foci are fla, flb. Preferably 0.75 mm≤fla≤5 mm, and 0.75 mm≤flb≤5 mm, where fla does not equal to flb. In some exemplary embodiments 1 mm≤fla≤2 mm, and 1 mm≤flb≤2 mm. More preferably 100 µm>|r1a−r1b|>10 µm. Preferably 1.5 mm>|fla−flb|>0.02 mm, for example, 1 mm>|fla−flb|>0.05 mm. Preferably, the distance d created between the two image spots (images of the core of the fiber 21, situated adjacent to the optical probe component 20) is at least 1 mm, preferably greater than 2 mm. In some embodiments r2<r1. In these embodiments, preferably, the radius r2 changes its value from r2a to r2b to provide the required depth of focus. Thus, in these embodiments r2a<r1a and r2b<r1b (to compensate for the aberrations introduced by the inner lumen 48).

Various embodiments will be further clarified by the following examples.

Example 1

Figure 4:
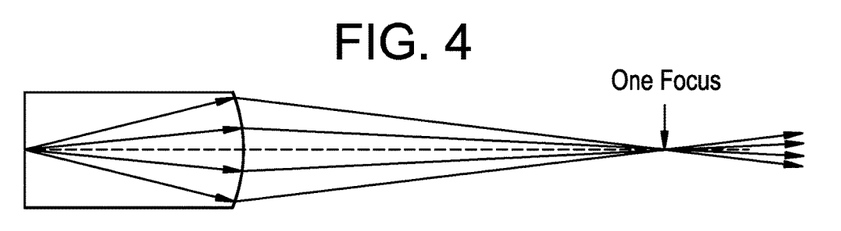
FIG. 4 shows a schematic cross-sectional (unfolded) view of a comparative optical probe component that has a refractive surface.

FIG. 4 illustrates an unfolded view of a refractive portion of a comparative micro component that has a 1.26 mm focal length and a 10 mm working distance. (This figure shows that the light is focused essentially in one spot (i.e., in one image plane). Thus, if an object or tissue that is being examined is located less or more than 10 mm away from the vertex of the curved refractive surface, the light provided by the micro optic components on the tissue will not be focused on the tissue.

Figure 5:
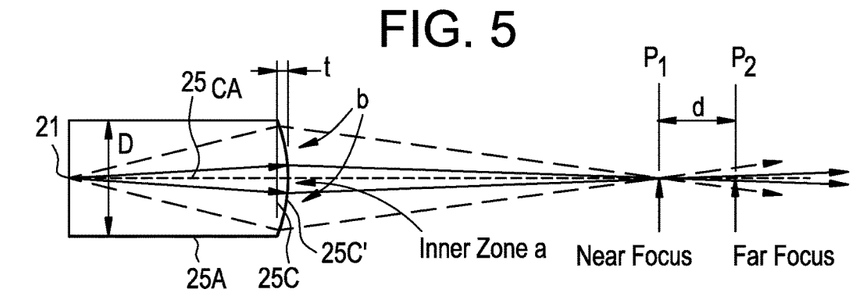
FIG. 5 shows a schematic cross-sectional (unfolded) view of one embodiment of the optical probe component that has a refractive surface.
Figure 6:
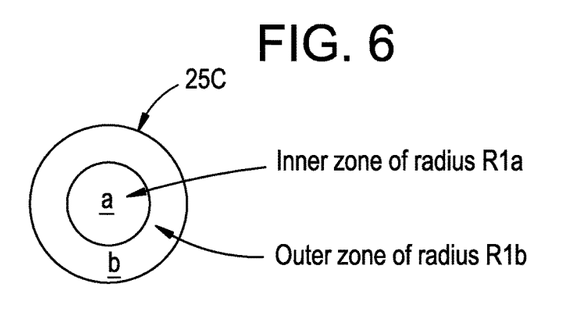
FIG. 6 illustrates another view of one embodiment of the refractive surface of optical probe component shown in FIG. 5.

FIG. 5 illustrates an unfolded view of a refractive portion of an exemplary multi-focal micro optic component 20 according to one embodiment. In this embodiment, the curved refractive surface 25C' includes multiple regions or zones—i.e., at least two regions an inner region a and an outer region b with different radii of curvature $r1_a$, $r1_b$. A small region (or zone c) situated in between regions a and b can also be present, for gradually changing the radius from $r1_a$ to $r1_b$, which would avoid scattered or diffracted light produced by the sudden change in radii from $r1_a$ to $r1_b$. (A surface discontinuity may result in large amount of back reflection and scattered light which would be detrimental to an OCT system.) In the example embodiment of FIG. 5 the radii r1a and r1b are very similar (less than 50 µm, e.g., 46 µm of one another. FIG. 5 illustrates (in at least one cross-sectional view) that the optical component 20 has two focal lengths fla (which corresponds to the radius r1a) and flb (which corresponds to the radius r1b) of 1.17 mm or the near focus and 1.26 mm for the far focus, and respective working distances wd (distances from the last surface of the micro opic component 20 and the images of the fiber core) of 6.8 mm and 11.1 mm. (That is, this figure shows that the light is focused in two spots on image planes P1 and P2.) Thus, if an object to be examined (or tissue) is between about 6.8 mm and 11.1 mm from the vertex of the refractive surface 25C', the light provided by the fiber core 21A will be imaged by the micro optic component 20 to form an image spot on the tissue. It is noted that the shortest wd>fla and wd>flb. Preferably, the shortest wd is at least twice as big as fla and fla. In this embodiment the shortest wd>4×Fla, and more specifically greater than 5 times Fla. FIG. 6 illustrates the front view of the lens surface 25C' of the optical component 20 according to this embodiment. As shown, the micro optic components 20 includes a split aperture non-diffractive lens 25C (and/or a split aperture (zones a and b) refractive surface 25C').

Figure 7A:
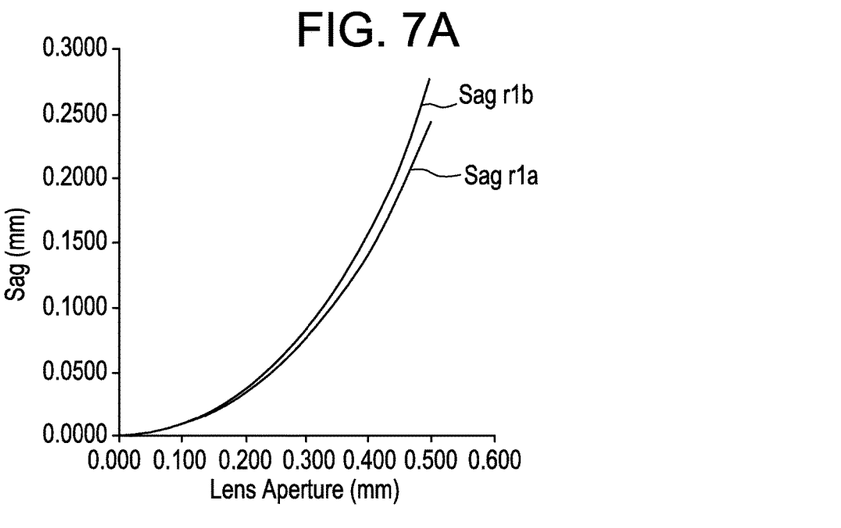
FIG. 7A is a plot of surface sag or the surface departure from the vertex, associated with radii r1a and r1b.
Figure 7B:
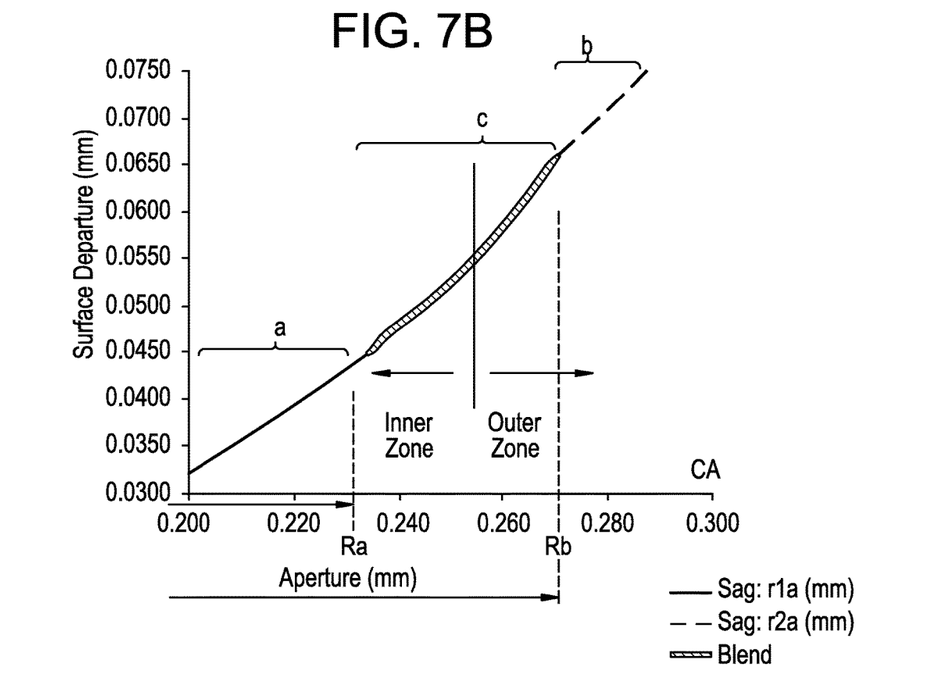
FIG. 7B is a plot of the exemplary surface sag (surface departure from the surface vertex, as a function of lens aperture) for at least a portion of one cross-section of the refractive surface shown in FIGS. 5 and 6.

FIG. 7A is a plot of surface sag or the surface departure from the vertex (due to radii $r1_a$ and r1b) or the surface departure from the vertex, if both are plotted from the vertex or the lens surface's center. Thus, if the lens surface has a sag determined by the radius $r1_a$ the surface sag will change when the radius of curvature changes to $r1_b$. FIG. 7B is a plot of the exemplary surface sag (surface departure from the surface vertex, as a function of lens aperture) for at least a portion of one cross-section of the refractive surface of the 25C' shown in FIGS. 5 and 6.

Figure 8:
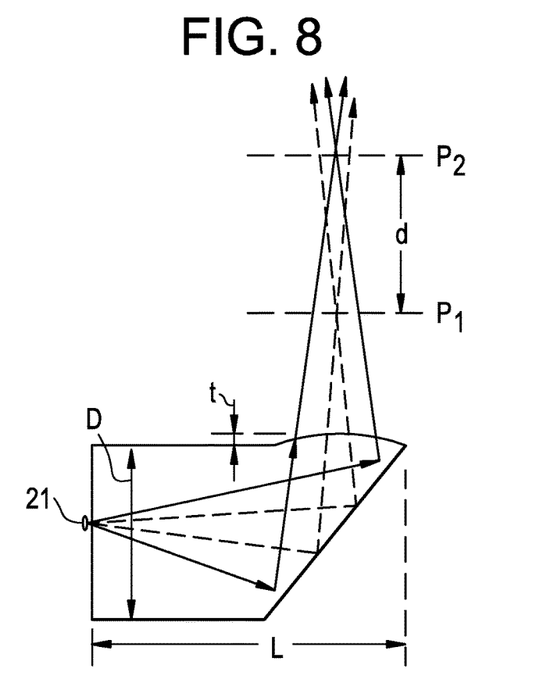
FIG. 8 illustrates schematically one embodiment of the multi-focal micro optic component that forms multiple image spots separated by a predetermined distance.

FIG. 8 illustrates one embodiment of the micro optic components 20 that includes a lens 25C with a refractive surface including two aperture zones a and b, characterized by with their respective radii of curvature $r1_a$, $r1_b$, and their respective focal lengths fla and flb. FIG. 8 illustrates that the image planes P1, P2 that are spaced apart by a distance d. More specifically, because surface 25C' includes an inner zone a, an outer zone b, and a transitional zone, the micro optic components 20 is multi-focal, and thus forms multiple image spots, as shown in FIG. 8. The two image spots formed on planes P1 and P2 (corresponding to zones a and b) are separated by a distance d, so a tissue located near or between these spots will be illuminated, and the backscattered light from the tissue would be collected back by the micro optic component 20 and provided back to the fiber 21 after it passes through surface 25C' and reflected back by the surface 25B towards the fiber 21. Preferably the distance d is at least 1 mm, preferably at least 2 mm, for example 2 mm to 15 mm. In some embodiments 0.75 mm≤fla≤5 mm, and 0.75 mm≤flb≤5 mm, where fla does not equal to flb. In some exemplary embodiments 1 mm≤fla≤2 mm, and 1 mm≤flb≤2 mm. More preferably 100 µm>|r1a−r1b|>10 µm. In some embodiments 1 mm>|fla−flb|>0.05 mm. In this embodiment the optical probe component 20 preferably has a length L (measured from the fiber facing surface to furthest surface (surface near the lens and/or the slanted surface), where 3 cm>L>0.3 cm (preferably, 2 cm>L>0.3 cm, for example 1.5 cm>L>0.3 cm or 1. cm>L>0.3 cm and the spacer rod 25A has a maximum diameter D (or maximum cross-section in the plane perpendicular to its optical axis)≤2 mm, and preferably ≤1.5 mm (for example, ≤1 mm). The maximum preferred overall length L' of the optical component 20 (including fiber mount 27 if it is integral thereto) is 3 cm>L'>0.5 cm, and preferably 2 cm>L'>0.5 cm, for example 1 cm>L'>0.5 cm.

Figure 9:
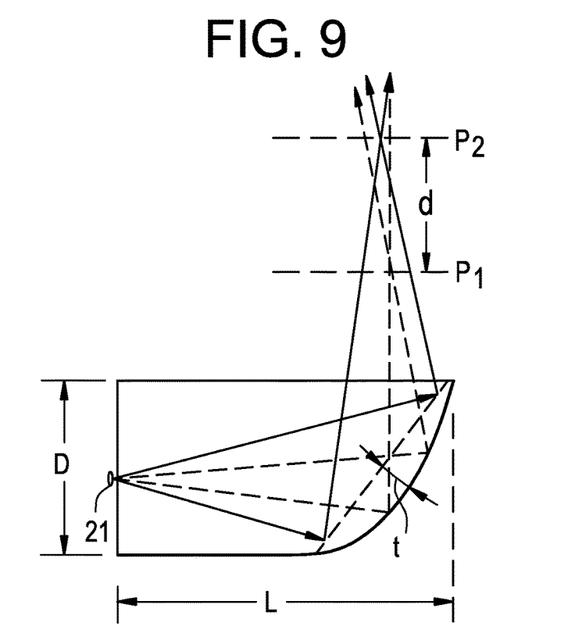
FIG. 9 illustrates schematically another embodiment of the multi-focal micro optic component that forms multiple image spots separated by a predetermined distance.

FIG. 9 is another embodiment of the micro optic components 20. The micro optic components 20 of this embodiment does not has a raised lens 25C, but the surface 25B that slanted with respect to the central axis $25_{C4}$, is curved and provides optical power. A reflective coating 25B' makes surface 25B a reflective surface. Accordingly, the curved surface 25B of the embodiment shown in FIG. 9 provides both the reflective and imaging function. In this embodiment the curved surface 25B includes at least two aperture zones, with their respective radii of curvature $r1_a$, $r1_b$, and respective focal lengths fla and flb, and image planes P1 and P2. The light from an object (fiber core 21A) propagates through the rod portion of the micro optic components 20, impinges on the curved surface and 25B and is reflected and reimaged. Because surface 25B inner zone a, an outer zone b, and a transitional zone, the micro optic components 20 is multifocal, it forms multiple image spots, as shown in FIG. 9. The two image spots formed on planes P1 and P2 (corresponding to zones a and b) are separated by a distance d, so a tissue located near or between these spots will be illuminated, and the back-scattered light from the tissue would be collected back by the micro optic component 20 and provided back to the fiber 21 after reflection from surface 25B. Preferably the distance d is at least 1 mm, preferably at least 2 mm, for example 2 mm to 15 mm. In some embodiments 0.75 mm≤fla≤5 mm, and 0.75 mm≤flb≤5 mm, where fla does not equal to flb. In some exemplary embodiments 1 mm≤fla≤3 mm, and 1 mm≤flb≤3 mm, and in some embodiments 1 mm≤fla≤2 mm, and 1 mm≤flb≤2 mm. In some exemplary embodiments 1 mm>|fla−flb|>0.05 mm. In this embodiment the optical probe component 20 preferably has a length L, where 3 cm>L>0.3 cm (preferably, 2 cm>L>0.3 cm, for example 1.5 cm>L>0.3 cm or 1. cm>L>0.3 cm, and the spacer rod 25A has a maximum diameter (or maximum cross-section D in the plane perpendicular to its optical axis)≤2 mm, and preferably ≤1.5 mm (for example, ≤1 mm).

More specifically, in general, a single mode light beam provided by the single mode fiber 21 can be used for imaging throughout the Rayleigh range to provide a spot of light on the tissues under examination. The Rayleigh range is defined by the following formula $z_R = \pi \omega_0^3/\lambda$, where wo is the spot radius (usually at $1/e^2$ or Peterman II) and lambda is the wavelength. Thus, in a system where a spot size is 33 μm in diameter at $1/e^2$ at a wavelength of 1310 nm, the rayleigh range would be 2.61 mm. Preferably, the to achieve the maximum usable depth of field, the images spots (and thus image planes P1, P2) image provided by the imaging portions of the micro optic component 20 should be separated by the sum of their rayleigh distances.

In the exemplary embodiment of FIG. 8, the object is the core 21A of the fiber 21, which is situated adjacent to the optic component 20 (e.g., SMF-28E® fiber core). This fiber core emits a single Gaussian mode with a diameter of 9.2 μm at $1/e^2$. In this embodiment the fiber 21 is glued to the micro optic component 20. The glue has index matched to the micro optic component 20 and has a thickness is about 0.1 mm. The light (in this embodiment at 1310 nm) provided by the fiber core then expands as it traverses through the thickness of the micro optic component 20 (i.e., through 2.01 mm of material with a refractive index of 1.5, at 1310 nm). After expanding from the fiber core, the light is refracted by the surface 25C' as it passes through the split aperture (i.e., multiple zones of different radii of curvature). One portion of the lens aperture had a surface defined by the radius of curvature $r1_a$=0.590 mm and the other corresponds to the surface portion defined by the radius of curvature $r1_b$=0.635 mm. Light passing through a portion of the lens surface 25C' with a radius of curvature r1a would focus (converge) to a closer working distance than the light passing through a portion of the lens surface that has the radius of curvature r1b. The two image spots or image planes P1, P2 are separated by about 4.27 mm. The farther spot would have a mode field diameter of about 76.6 μm and the closer spot would have a mode field diameter of about 45.4 μm. The Rayleigh range of the closer focus (on image plane) would be +/−1.23 mm and +/−3.52 mm for the far focus (far imaged plane). This would give a large depth of focus of 9.02 mm. To increase the power density, the radii could be closer together, thereby bringing the foci and image planes closer, and making the spot sizes more similar in diameter.

Modeled optical parameters for one embodiment of the optical probe that includes optical component 20 shown in FIG. 8 are provided in Table 1, below. In this table, Surface #0 corresponds to the fiber core that is being imaged at the tissue (image surface). Surface #1 corresponds to the adhesive surface facing the fiber, and the thickness 0.1 mm is the adhesive's thickness. Surface #2 is corresponds to the end surface of the rod that is facing the fiber. Surface #3 corresponds to the tilted reflective surface 25B, and Surface #4. corresponds to the lens surface 25C'. All the thicknesses (in mm) are measured from the given surface to the next surface. Thus, thickness 6.83 mm and 11.1 mm correspond to the distances from the vertex of Surface #4 (I.e., from the vertex of the lens surface 25C' to the image planes—these are the working distances wd, associated with the corresponding radii of curvature r1a=0.59 mm (zone a) and r2a=0.635 mm (zone b)). Please note that in this embodiment, Surface #2 is tilted by 8° with respect to the optical axis if the rod 25A, and that the reflective surface 25B is tilted by 40.1° with respect to the optical axis. The optical probe component 20 of Table 1 was not intended to be utilized with the cylindrical inner lumen, thus surface 25C' is rotationally symmetrical. Also, in this embodiment the end surface of fiber 21 is cleaved at an 8° relative to the fiber axis and relative to the axis of the rod 25A. Thus, in Table1, Surface #0 is shown tilted at 8°.

TABLE 1 optical parameters

| Surface # | $\theta_S$ | Thickness (mm) | Material | $R_{1a\ (mm)}$ | $R_{1b\ (mm)}$ | $R_{2a\ (mm)}$ | $R_{2b\ (mm)}$ |
|---|---|---|---|---|---|---|---|
| 0-Fiber | 8 | — | — | ∞ | ∞ | | |
| 1 | 0 | 0.1 | Adhesive | ∞ | ∞ | | |
| 2 | 8 | 1.5 | Plastic N = 1.5@1300 nm | ∞ | ∞ | | |
| 3 | 40.1 | 0.5 | Plastic N = 1.5@1300 nm | ∞ | ∞ | | |
| 4 | 0 | 6.83, 11.1 | Air | 0.590 | 0.635 | 0.590 | 0.635 |
| Image Plane | 0 | — | Air | ∞ | ∞ | | |

Figure 10:
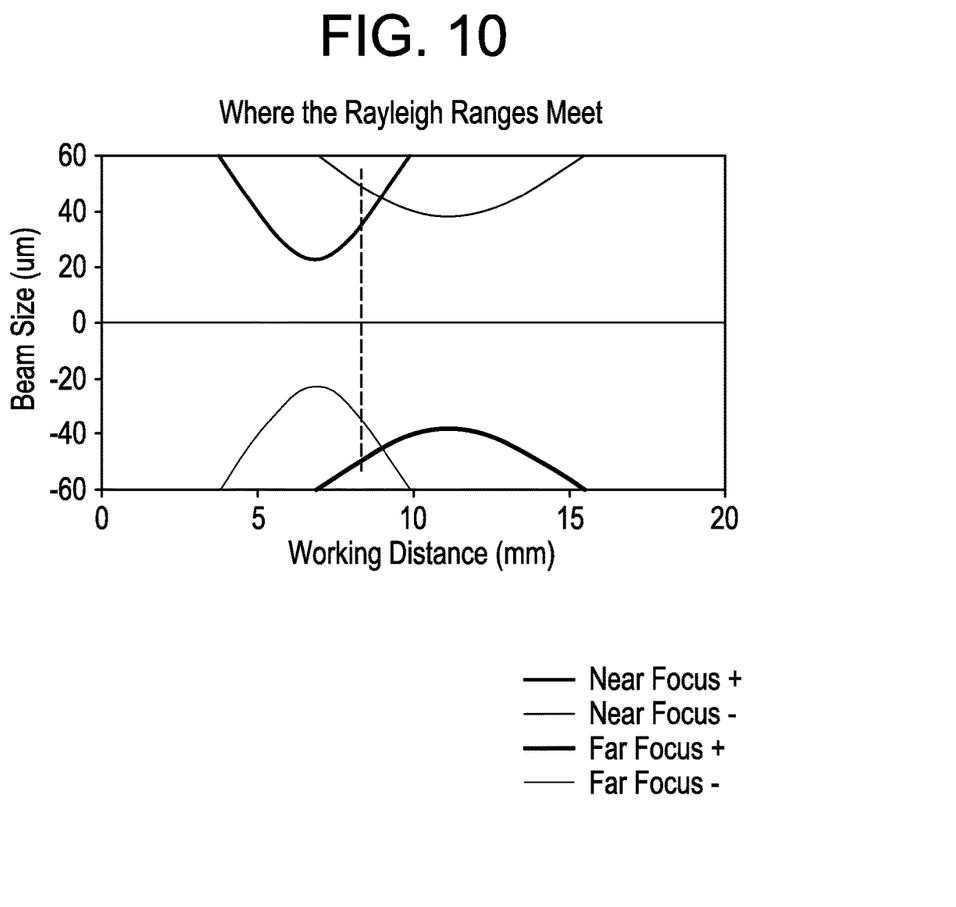
FIG. 10 is a plot of beam diameters vs. working distances for the near and far foci of one embodiment of multi-focal micro optic component.

FIG. 10 is a plot of beam sizes vs working distances for the near and far foci of one embodiment of multi-focal micro optic component. More specifically, FIG. 10 illustrates how the beam diameter from each refraction zone would propagate as a function of distance from the lens vertex.

Thus, according to some embodiments, an optical probe component for OCT comprises: (a) a rod 25A having a first end 20A' (situated near the optical fiber 21); (b) a lens situated to be optically coupled to the rod (e.g., situated proximate to and/or integral with the rod), the lens having a surface with an inner zone a, and an outer zone b, wherein said inner zone corresponds to a focal length fla, and said outer zone is corresponds to the focal length flb, such that said optical probe component is multi-focal. The optical probe 20 is capable of imaging via the lens (25C (as shown, for example, in FIG. 8), $25C_G$ (as shown, for example in FIG. 3), or 25B (as shown, for example, in FIG. 9)) an object (fiber core 21A) adjacent to the first end 20A' of the spacer rod at multiple image planes, wherein at least two images are separated by a distance d, wherein d>1 mm. In some embodiments the lens element is a GRIN lens. In some embodiments (see for example FIGS. 8 and 9) the lens element is a refractive lens with at least one a curved surface that provides optical power, and the curved surface has an inner zone a defined by the radius of curvature r1a and an outer zone b defined by a radius of curvature r1b, wherein r1a is not equal to r1b. In the embodiments disclosed herein 100 µm≤r1a. Preferably, 100 µm≤r1a≤5000 µm; 100 µm≤r1b≤5000 µm; and |r1a−r1b|>2 µm. According to some embodiments and 500 µm>|r1a−r1b|>10 µm. According to some embodiments the curved surface is slanted with respect to the optical axis of the rod 25A, and has a reflective coating. According to these embodiments the optical probe component 20 has a length L, where 3 cm>L>0.5 cm (preferably, 2 cm>L>0.5 cm, for example 1.5 cm>L>0.5 cm and the rod 25A preferably has a maximum diameter (or maximum cross-section in the plane perpendicular to its optical axis)≤2 mm, and preferably ≤1.5 mm (for example, ≤1 mm). Preferably, in at least one cross-section, 1.5 mm>|fla−flb|>0.02 mm, for example, 1 mm>|fla−flb|>0.05 mm. Preferably, the distance d created between the two image spots (images of the core of the fiber 21, situated adjacent to the optical probe component 20) is at least 1.5 mm, preferably at least 2 mm. In some embodiments r2a<r1a and r2b<r1b (to compensate for the aberrations introduced by the inner lumen 48). It is also noted that in these embodiments, in at least one cross-section, the working distance wd (distance from the optical surface of the optical probe component 20 and the closest image of the fiber's core) is much greater than the focal lengths fla, flb. For example, wd>2×fla and wd>2×flb, and preferably wd≥3×fla. In some embodiments, wd≥4×fla, or wd≥5×fla.

Modeled optical parameters for one embodiment of the optical probe that includes optical component 20 similar to that shown in FIG. 2 are provided in Table 2, below. In this table, Surface #0 corresponds to the fiber core 21A that is being imaged at the tissue (image surface). Surface #1 is corresponds to the end surface of the rod 25A that is facing the fiber. Surfaces #2 corresponds to first surface of the GRIN lens $25C_G$—i.e., to the surface of the GRIN lens that is facing the rod 25A), Table 2 lists Surface #2 values for both zone a and zone b. Surface #3 is the surface of the prism facing the GRIN lens $25C_G$, and Surface #4 corresponds to the reflective surface of the prism $25B_P$. All the thicknesses (in mm) are measured from the given surface to the next surface. Please note that in this embodiment, Surface #1 is tilted by 8° with respect to the optical axis if the rod 25A.

Also, in this embodiment the end surface of fiber 21 is cleaved at an 8° relative to the fiber axis and relative to the axis of the rod 25A. Thus, in Table 2, Surface #0 is also shown tilted at 8°. Table 2. The two image planes P1 and Ps associated with zones a and b respectively are located 13.49 mm and 11 mm away from the prism's surface. That is, in the embodiment of Table 2, the distance d is about 2.5 mm.

TABLE 2 optical probe with a two zone GRIN lens $25C_G$

| Surface # | $\theta_S$ (degrees) | Thickness (mm) | Material Index/ Gradient Constant | Radius |
|---|---|---|---|---|
| 0- Fiber core 21A | 8 | — | — | ∞ |
| 1 - Spacer/rod 25A | 8 | 2.95 | Fused Silica | ∞ |
| 2 - GRIN (inner zone a) | 0 | 0.752 | Base index 1.46 Gradient Constant = 0.69 mm$^{-1}$ | ∞ |
| 2- GRIN (outer zone b) | 0 | 0.752 | Base index 1.46 Gradient Constant = 0.70 mm$^{-1}$ | ∞ |
| 3 - first surface of Prism $25B_P$ | 0 | 1 | Fused Silica | ∞ |
| 4- Prism reflecting surface | 40-45 | 0.5 | Fused Silica | ∞ |
| 5 - Image plane (inner zone a) | 0 | 13.49 | Air | ∞ |
| 5 - Image plane (outer zone b) | 0 | 11 | Air | ∞ |

Figure 1:
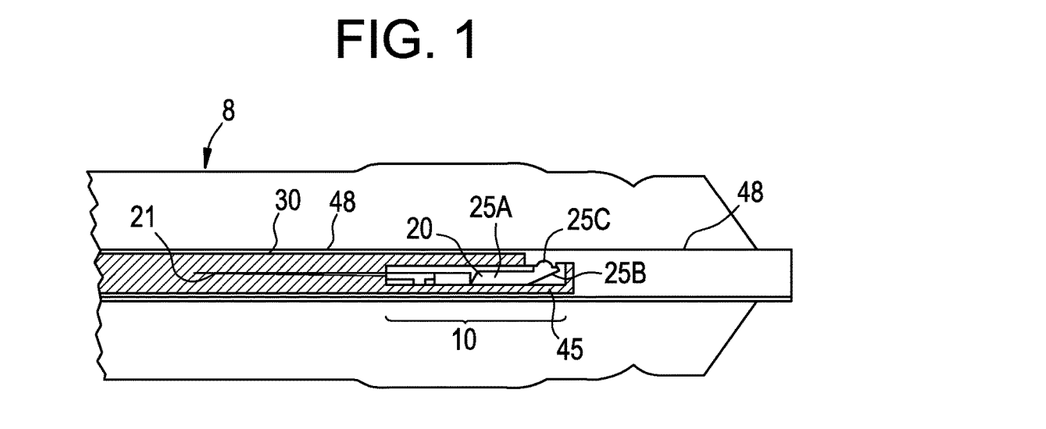
FIG. 1 is a schematic cross-sectional view of one embodiment of OCT probe.

Therefore, according to some embodiments, the OCT probe 5 comprises the multi-focal optical probe component 20 capable of producing at least two images that are separated by a distance d, wherein d>1 mm as described above, and further includes an optically transparent cylinder e.g., an inner lumen 48, or an optically transparent window) surrounding or covering at least a portion of the optical probe component. According to some embodiments, the OCT probe 5 also comprises housing 45 for the optical probe component 20. The housing 45 surrounds at least a portion of the OCT optical probe component. As shown in FIG. 1, the housing 45 may be positioned between the optically transparent cylinder and the optical probe component 20. As shown in FIG. 1, the OCT probe 5 also includes an optical fiber 21 for providing light to the optical probe component 20, and a torque tube or another rotation/translation device. The maximum preferred overall length L' of the optical component 20 (including fiber mount 27 if it is integral thereto) is 3 cm>L'>0.5 cm, and preferably 2 cm>L'>0.5 cm, for example 1 cm>L'>0.5 cm.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. An OCT optical probe component comprising: (a) rod; (b) and a curved refractive surface, said curved refractive surface having an inner zone a defined by the radius of curvature r1a and an outer zone b defined by a radius of curvature r1b, wherein r1a is not equal to r1b and the optical probe component is multi-focal.

2. The OCT optical probe component according to claim 1, wherein 100 µm≤r1a≤5000 µm; 100 µm≤r1b≤5000 µm; and |r1a−r1b|>2 µm.

3. The OCT optical probe component according to claim 1, wherein 100 µm≤r1a≤2500 µm; 100 µm≤r1b≤2500 µm; and |r1a−r1b|>10 µm.

4. The OCT optical probe component according to claim 1, wherein 100 µm≤r1a≤2500 µm; 100 µm≤r1b≤2500 µm; and 500 µm>|r1a−r1b|>10 µm.

5. The OCT optical probe component according to claim 1, wherein the OCT optical probe component has the length L wherein 2 cm>L>0.5 cm and the rod has a maximum diameter<2 mm.

6. The OCT optical probe component according to claim 2, wherein the OCT optical probe component has the length L wherein 2 cm>L>0.5 cm and the rod has a maximum diameter<2 mm.

7. The OCT optical probe component according to claim 1, said curved refractive surface in one cross-section has at least two zones defined by the radii r1a and r1b wherein 100 µm≤r1a≤5000 µm; 100 µm≤r1b≤5000 µm; and |r1a−r1b|>2 µm; and in another cross-section is defined by at least one radius r2, such that r2>r1a and r2>r1b.

8. The OCT optical probe component according to claim 1 wherein if an object is located proximate to one surface of the rod, it is reimaged in at least two locations separated by a distance d, such the distance d≥1 mm.

9. The OCT optical probe component according to claim 1 wherein if an object is located proximate to one surface of the rod, it is reimaged in at least two locations separated by a distance d, such the distance d≥2 mm.

10. The OCT optical probe component having a first end a second end and comprising:
a second end, a second end, and
(a) a light transmissive rod having a central axis;
(b) a reflective surface situated on the second end and slanted with respect to the central axis;
(c) a lens element situated on the rod and being integral there to, and adjacent to the second end, the lens element having a curved refractive surface, said curved refractive surface having an inner zone a defined by the radius of curvature r1a and an outer zone b defined by a radius of curvature r1b, wherein r1a is not equal to r1b and the optical probe component is multi-focal.

11. The OCT optical probe component according to claim 10 wherein 100 µm≤r1a≤5000 µm; 100 µm≤r1b≤5000 µm; and |r1a−r1b|>2 µm.

12. The OCT optical probe component according to claim 10 wherein an object located proximate to one surface of the rod is imaged in at least two locations separated by a distance d, such the distance d>2 mm, and the optical probe component has a focal length f1a associated with the inner zone, wherein working distance wd between the OCT optical probe component and the nearest image is at least 2 times f1a.

13. An OCT optical probe component comprising:
a. an optically transparent rod having a first end, and
b. a lens optically coupled to the rod, said lens having a surface with an inner zone a, and an outer zone b, wherein said inner zone corresponds to a focal length fa, and said outer zone is associated with the focal length fb, such that said optical probe component is multi-focal, said optical probe capable of imaging via the lens an object adjacent to the first end of said spacer rod at multiple image surfaces, wherein at least two images are separated by a distance d, wherein d>1 mm.

14. An OCT optical probe component of claim 13, wherein said lens is a GRIN lens, or said lens has a curved surface and reflective coating situated thereon.

15. The OCT probe component of claim 13, wherein said lens is a refractive lens with at least one a curved surface, and the curved surface has an inner zone a defined by the radius of curvature r1a and an outer zone b defined by a radius of curvature r1b, wherein r1a is not equal to r1b.

16. The OCT optical probe component according to claim 13, wherein 100 µm≤r1a≤5000 µm; 100 µm≤r1b≤5000 µm; and |r1a−r1b|>2 µm.

17. The OCT optical probe component according to claim 13 wherein d>2 mm, and the optical probe component has a focal length f1a associated with the inner zone, wherein working distance wd between the OCT optical probe component and the nearest image at least 2 times f1a.

18. An OCT probe comprising the OCT optical probe component of claim 13, further comprising, an optically transparent cylinder surrounding at least a portion of the OCT optical probe component.

19. The OCT probe further according to claim 18 further comprising: a housing surrounding at least a portion of the OCT optical probe component, the housing being positioned between the optically transparent cylinder and the OCT optical probe component.

20. The OCT probe according to claim 18 further comprising: a fiber optically coupled to the OCT optical probe component, and a rotation/translation device attached to the OCT optical probe component.

* * * * *